US012635935B2

(12) United States Patent
    Osuga et al.

(10) Patent No.:  US 12,635,935 B2
(45) Date of Patent:      May 26, 2026

(54) INFORMATION PROCESSING APPARATUS, INFORMATION PROCESSING METHOD, NON-TRANSITORY COMPUTER-READABLE STORAGE MEDIUM WITH EXECUTABLE INFORMATION PROCESSING PROGRAM STORED THEREON, AND INFORMATION PROCESSING SYSTEM

(71) Applicant: Noriyuki Minami, Kyoto (JP)

(72) Inventors: Seiya Osuga, Kyoto (JP); Junichi Takatori, Kyoto (JP)

(73) Assignee: NINTENDO CO., LTD., Kyoto (JP)

( * ) Notice: Subject to any disclaimer, the term of this patent is extended or adjusted under 35 U.S.C. 154(b) by 401 days.

(21) Appl. No.: 17/355,928

(22) Filed: Jun. 23, 2021

(65) Prior Publication Data

US 2021/0315519 A1      Oct. 14, 2021

Related U.S. Application Data

(63) Continuation of application No. PCT/IB2019/061353, filed on Dec. 25, 2019.

(30) Foreign Application Priority Data

Dec. 28, 2018    (JP) ................................. 2018-248121

(51) Int. Cl.
    *A61B 5/00*          (2006.01)
    *G01S 13/56*          (2006.01)
            (Continued)

(52) U.S. Cl.
    CPC ............ *A61B 5/4812* (2013.01); *G01S 13/56* (2013.01); *G01S 13/88* (2013.01); *G08B 21/06* (2013.01);
            (Continued)

(58) Field of Classification Search
    CPC .......... A61B 5/4812; A61B 2562/0257; G16H 40/67; G01S 13/56; G01S 13/88; G08B 21/06
    See application file for complete search history.

(56)              References Cited

U.S. PATENT DOCUMENTS

2004/0046736 A1*    3/2004    Pryor ..................... G16H 50/50
                                                              345/156
2013/0053653 A1      2/2013    Cuddihy et al.
                    (Continued)

FOREIGN PATENT DOCUMENTS

EP            2 417 908          2/2012
JP        2010120493 A        6/2010
                (Continued)

OTHER PUBLICATIONS youtubeRef1.pdf, Withings, screenshot at 0:47, https://www.youtube.com/watch?v=GB2yFdu1vwo, Withings, (Year: 2018).*
                (Continued)

*Primary Examiner* — William Kelleher
*Assistant Examiner* — Kenneth W Good
(74) *Attorney, Agent, or Firm* — Nixon & Vanderhye PC

(57)              ABSTRACT

A new configuration in which a distance to a user in addition to a sleep state of the user is measured is provided. An information processing apparatus includes a sensing unit including a Doppler sensor, a distance measurement unit that measures a distance to a user based on an output from the Doppler sensor, and a sleep state measurement unit that measures in real time, a sleep state of the user based on the output from the Doppler sensor.

20 Claims, 19 Drawing Sheets

(51) Int. Cl.

| | |
|---|---|
| *G01S 13/88* | (2006.01) |
| *G08B 21/06* | (2006.01) |
| *G16H 40/67* | (2018.01) |

(52) U.S. Cl.

CPC ...... *G16H 40/67* (2018.01); *A61B 2562/0257* (2013.01)

(56) References Cited

U.S. PATENT DOCUMENTS

| | | | |
|---|---|---|---|
| 2014/0276245 | A1 | 9/2014 | Tsutsumi et al. |
| 2017/0136348 | A1* | 5/2017 | Hattori .................. A61B 5/742 |
| 2018/0289332 | A1 | 10/2018 | Yamaji et al. |
| 2019/0053707 | A1* | 2/2019 | Lane ...................... G16H 40/67 |
| 2019/0133499 | A1* | 5/2019 | Auerbach ............ A61B 5/7282 |
| 2019/0271763 | A1* | 9/2019 | Grabbe .................. G06Q 10/08 |
| 2019/0293776 | A1* | 9/2019 | Yokoi .................... G01S 13/86 |
| 2019/0379386 | A1* | 12/2019 | Chi ...................... G01S 7/4004 |
| 2020/0100055 | A1* | 3/2020 | Pham ...................... H04W 4/90 |
| 2021/0150873 | A1* | 5/2021 | Shouldice .............. G06F 21/32 |
| 2021/0197834 | A1* | 7/2021 | Shaker .................. G06V 40/25 |
| 2021/0361225 | A1* | 11/2021 | Dunn ...................... A61B 5/01 |
| 2022/0007965 | A1* | 1/2022 | Tiron .................. A61B 5/0823 |

FOREIGN PATENT DOCUMENTS

| | | | |
|---|---|---|---|
| JP | 2011102783 | A | 5/2011 |
| JP | 2013-94340 | | 5/2013 |
| JP | 2014-14708 | | 1/2014 |
| JP | 2016045045 | A | 4/2016 |
| WO | 2012/008264 | | 1/2012 |
| WO | 2014/159773 | A1 | 10/2014 |
| WO | 2017098609 | A1 | 6/2017 |
| WO | WO-2018033574 | A1 * | 2/2018 ........... A61B 5/7225 |

OTHER PUBLICATIONS

"Omnidirectional Time Meter Handling Instructions", OMRON, SleepDesign Lite Instruction Manual, Sep. 23, 2017, 5 pages.

International Search Report for PCT/IB2019/061353 dated Mar. 17, 2020, 5 pages with English Translation.

Written Opinion of the ISA for PCT/IB2019/061353 dated Mar. 17, 2020, 2 pages with Machine Translation.

* cited by examiner

PRESENCE SCORE ≠ 0

MOTION INTEGRATED VALUE

DISTANCE
(index)

PRESENCE SCORE = 0

MOTION INTEGRATED VALUE

DISTANCE
(index)

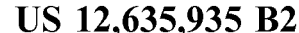

ST1

ABSENCE

CONDITION FOR TRANSITION FROM
GOTTEN UP ⇒ ABSENCE
CONDITION FOR TRANSITION FROM
LYING TO SLEEP ⇒ ABSENCE
CONDITION FOR TRANSITION FROM
REST ⇒ ABSENCE
·PRESENCE SCORE < TH2 CONTINUES
FOR PRESCRIBED TIME PERIOD
TR3

CONDITION FOR TRANSITION FROM
ABSENCE ⇒ GOTTEN UP
·PRESENCE SCORE > TH1 CONTINUES
FOR PRESCRIBED TIME PERIOD
OR
·SLEEP STATE = WAKE

TR1

TR2

CONDITION FOR TRANSITION
FROM GOTTEN UP ⇒ REST
· REST DETERMINATION CONDITION BEING SATISFIED

ST2

GOTTEN UP

TR5

TR6

ST4

REST

ST3

CONDITION FOR
TRANSITION FROM
GOTTEN UP ⇒ LYING TO SLEEP
·LYING-TO-SLEEP DETERMINATION
CONDITION BEING SATISFIED

TR8

TR7

CONDITION FOR TRANSITION FROM REST
⇒ GOTTEN UP
· REST DETERMINATION CONDITION
NOT BEING SATISFIED

TR9

CONDITION FOR TRANSITION
FROM REST ⇒ LYING TO SLEEP
·LYING-TO-SLEEP DETERMINATION
CONDITION BEING SATISFIED

CONDITION FOR TRANSITION
FROM LYING TO SLEEP ⇒ GOTTEN UP
·LYING-TO-SLEEP DETERMINATION
CONDITION NOT BEING SATISFIED
OR
·SLEEP STATE = WAKE

LYING TO SLEEP

ST4

CND1

REST DETERMINATION
CONDITION

· (BODY MOTION SCORE < TH4 AND PRESENCE SCORE
> TH1) CONTINUES FOR PRESCRIBED TIME PERIOD

NOT
SATISFIED

SATISFIED

· BODY MOTION SCORE > TH3 OR PRESENCE SCORE
< TH1

CND2

LYING-TO-SLEEP
DETERMINATION
CONDITION

· SLEEP STATE = SLEEP (LIGHT SLEEP, DEEP SLEEP, OR
REM SLEEP) CONTINUES FOR PRESCRIBED TIME PERIOD

NOT
SATISFIED

SATISFIED

· SLEEP STATE ≠ SLEEP (LIGHT SLEEP, DEEP SLEEP,
OR REM SLEEP)

MEASUREMENT TARGET

INFORMATION PROCESSING APPARATUS, INFORMATION PROCESSING METHOD, NON-TRANSITORY COMPUTER-READABLE STORAGE MEDIUM WITH EXECUTABLE INFORMATION PROCESSING PROGRAM STORED THEREON, AND INFORMATION PROCESSING SYSTEM

This application is a continuation of International Application No. PCT/IB2019/061353 filed on Dec. 25, 2019, which claims priority to Japanese Application No. 2018-248121 filed on Dec. 28, 2018, the entire contents of each of which are hereby incorporated by reference herein.

FIELD

The present disclosure relates to a method of measuring a sleep state of a user based on an output from a Doppler sensor.

BACKGROUND AND SUMMARY

A technique for processing a biological signal such as breath, heartbeat, and body motion of a user to determine depth of sleep of a living body has conventionally been proposed.

The conventional technique is on the premise that a sleep state of a single user is determined, and has paid no attention to a distance to the user. An object of the present disclosure is to provide a new configuration in which a distance to a user in addition to a sleep state of the user is measured.

An information processing apparatus according to one embodiment includes a sensing unit including a Doppler sensor, a distance measurement unit that measures a distance to a user based on an output from the Doppler sensor, and a sleep state measurement unit that measures in real time, a sleep state of the user based on the output from the Doppler sensor.

According to the present configuration, an identical Doppler sensor can be used to measure in real time, a distance to a user and a sleep state of the user. Therefore, processing making use of results of measurement of both of the distance to the user and the sleep state of the user can be implemented.

The sleep state measurement unit may measure the sleep state of a user who is present within a prescribed area smaller than a measurement area within which the distance measurement unit is able to conduct measurement, based on a result of measurement by the distance measurement unit. According to the present configuration, for example, even when a plurality of users are sleeping, the sleep state only of the user who is present within the prescribed area can be measured. Therefore, such a situation that the sleep state of a user who is not a measurement target is erroneously measured can be avoided.

The information processing apparatus may further include a presence determination unit that determines whether or not the user is present based on the result of measurement by the distance measurement unit. The presence determination unit may determine the user as not being present based on the measured distance to the user being not within the prescribed area. According to the present configuration, for example, when a plurality of users are sleeping, determination as the user who is the measurement target having left the bed can appropriately be made.

The information processing apparatus may further include a guidance provider that provides guidance for assisting adjustment in advance of relative positional relation between a position where the information processing apparatus is placed and a position where the user lies during sleep. According to the present configuration, the user can arrange the information processing apparatus at an appropriate position in accordance with the guidance.

The guidance provider may provide output of at least one of an image and sound that indicates whether or not the position where the user lies is within the prescribed area. According to the present configuration, the user can visually or aurally know at which position the information processing apparatus should be arranged.

The information processing apparatus may further include a setting acceptor that accepts setting of the prescribed area from the user. According to the present configuration, an appropriate measurement target area can be set in accordance with an environment where the user lies.

The setting acceptor may request for input of at least one of a position where the user lies during sleep and the number of persons who lies therein. According to the present configuration, an appropriate measurement target area can be set in accordance with a state that the user lies during sleep.

The setting acceptor may change the prescribed area based on the result of measurement of the sleep state of the user. According to the present configuration, a measurement target area can appropriately be set based on a result of measurement for the user.

The information processing apparatus may further include a representation editor that has the result of measurement of the sleep state of the user shown and accepts an edition operation by the user onto the result of measurement. The setting acceptor may change the prescribed area in response to the edition operation accepted by the representation editor. According to the present configuration, a measurement target area can appropriately be adjusted in advance in response to an edition operation arbitrarily performed by the user.

The distance measurement unit may calculate an amount of motion at each distance from the Doppler sensor, based on the output from the Doppler sensor, and estimate a distance at which the amount of motion is largest as the distance to the user. According to the present configuration, a distance at which the user is highly likely to be present can be determined.

The distance measurement unit may focus, as the amount of motion, on motion by breathing by the user. According to the present configuration, even during sleep, the distance to the user can be measured.

According to another embodiment, an information processing method in an information processing apparatus including a sensing unit including a Doppler sensor is provided. The information processing method includes measuring a distance to a user based on an output from the Doppler sensor and measuring in real time, a sleep state of the user based on the output from the Doppler sensor.

According to the present configuration, an identical Doppler sensor can be used to measure in real time, a distance to a user and a sleep state of the user. Therefore, processing making use of results of measurement of both of the distance to the user and the sleep state of the user can be implemented.

According to yet another embodiment, an information processing program executed by a computer including a sensing unit including a Doppler sensor is provided. The information processing program causes the computer to perform measuring a distance to a user based on an output from the Doppler sensor and measuring in real time, a sleep state of the user based on the output from the Doppler sensor.

According to the present configuration, an identical Doppler sensor can be used to measure in real time, a distance to a user and a sleep state of the user. Therefore, processing making use of results of measurement of both of the distance to the user and the sleep state of the user can be implemented.

A system according to still another embodiment includes a sensing device including a Doppler sensor and a control device. The control device includes a distance measurement unit that measures a distance to a user based on an output from the Doppler sensor and a sleep state measurement unit that measures in real time, a sleep state of the user based on the output from the Doppler sensor.

According to the present disclosure, a new configuration in which a distance to a user in addition to a sleep state of the user is measured can be provided.

BRIEF DESCRIPTION OF THE DRAWINGS

FIG. 5 is a schematic diagram showing an exemplary form of use of the sleep alarm apparatus according to the present embodiment.

FIGS. 7A and 7B are diagrams for illustrating a scheme for measurement with a Doppler sensor of the sleep alarm apparatus according to the present embodiment.

FIG. 12 is a diagram for illustrating a method of determining a lying state in the sleep alarm apparatus according to the present embodiment.

DETAILED DESCRIPTION OF NON-LIMITING EXAMPLE EMBODIMENTS

Figure 1:
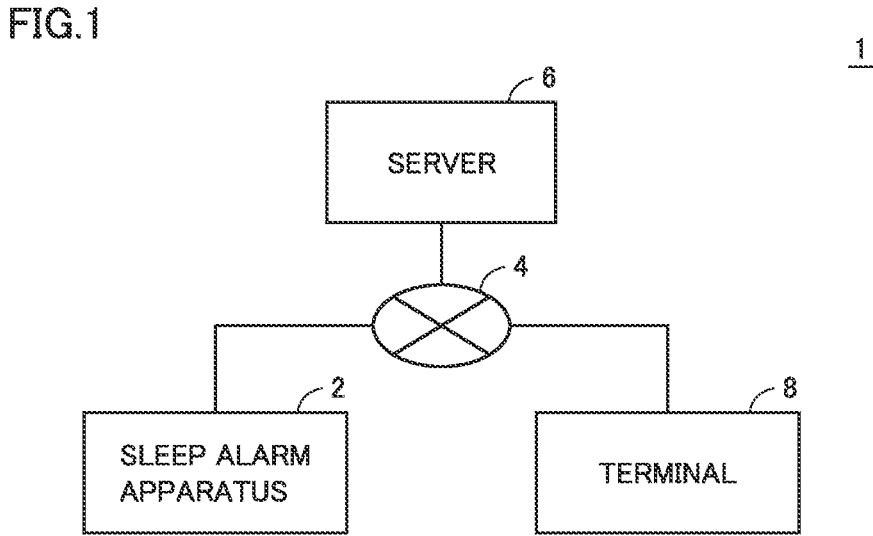
FIG. 1 is a schematic block diagram showing a basic configuration of a sleep management system according to the present embodiment.

The present embodiment will be described in detail with reference to the drawings. The same or corresponding elements in the drawings have the same reference characters allotted and description thereof will not be repeated.

An information processing apparatus in the present embodiment will be described as a sleep alarm apparatus by way of example. A portable (also referred to as mobile) apparatus or a stationary apparatus may be applicable.

[A. Configuration of Sleep Management System]

An exemplary configuration of the entire sleep management system 1 and each apparatus according to the present embodiment will initially briefly be described.

(a1: Sleep Management System 1)

FIG. 1 is a schematic block diagram showing a basic configuration of sleep management system 1 according to the present embodiment. Referring to FIG. 1, sleep management system 1 includes a sleep alarm apparatus 2, a network 4, a server 6, and a terminal 8.

Information can be transmitted and received among sleep alarm apparatus 2, server 6, and terminal 8 over network 4. Network 4 may adopt any of wireless communication and wired communication.

Sleep alarm apparatus 2 manages sleep of a user. Sleep alarm apparatus 2 performs an alarm function to wake the user up and a sensor function to contactlessly sense a signal depending on motion of the user. When a notification condition is satisfied, sleep alarm apparatus 2 performs a notification operation by output of alarm sound from a speaker or the like which represents an exemplary notification unit, and when a notification stop condition is satisfied, it stops output of alarm sound.

Sleep data obtained by sleep alarm apparatus 2 is stored in server 6.

Terminal 8 obtains setting for the alarm function of sleep alarm apparatus 2 and information on a sleep state of the user and shows them. Terminal 8 may be a portable (also referred to as mobile) apparatus such as a portable telephone or a smartphone or a stationary apparatus such as a personal computer.

(a2: Sleep Alarm Apparatus 2)

Figure 2:
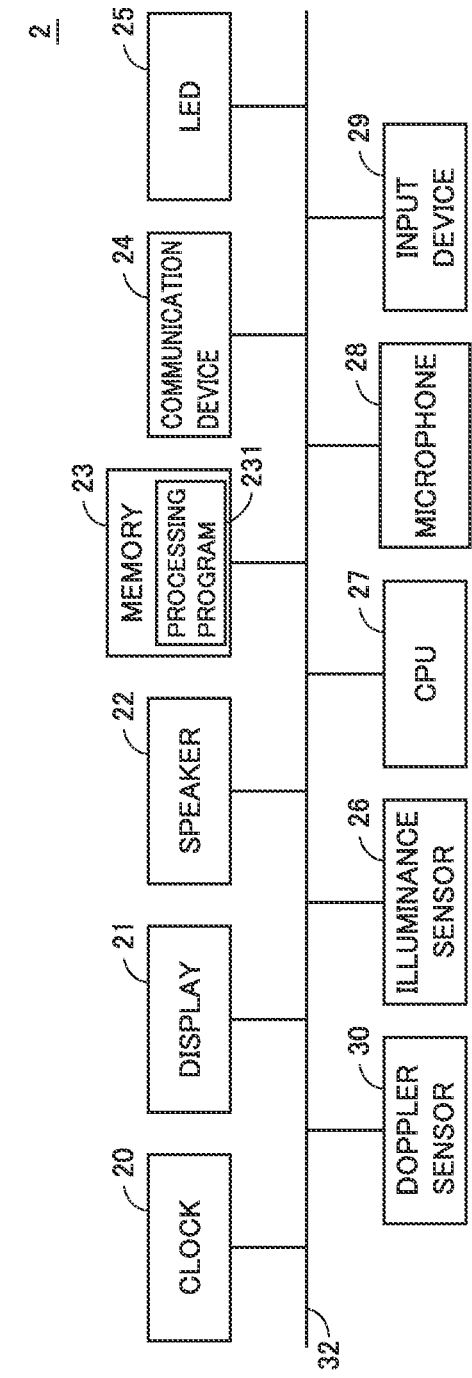
FIG. 2 is a schematic block diagram showing a basic configuration of a sleep alarm apparatus according to the present embodiment.

FIG. 2 is a schematic block diagram showing a basic configuration of sleep alarm apparatus 2 according to the present embodiment. Referring to FIG. 2, sleep alarm apparatus 2 includes a clock 20, a display 21, a speaker 22, a memory 23, a communication device 24, an LED 25, an illuminance sensor 26, a CPU 27, a microphone 28, an input device 29, a Doppler sensor 30, and an internal bus 32. Components are connected through internal bus 32.

CPU 27 represents one of processors and corresponds to an information processing unit for implementing various types of information processing performed in sleep alarm apparatus 2. CPU 27 performs various types of information processing by using memory 23.

A processing program 231 executed in sleep alarm apparatus 2 is stored in memory 23. Though FIG. 2 illustrates an example in which memory 23 serves as a storage contained in sleep alarm apparatus 2, for example, a storage medium attachable to and removable from sleep alarm apparatus 2 such as an optical disc or a cartridge may be applicable or both of the storage and the storage medium as such may be applicable.

CPU 27 implements processing and various functional blocks involved with various functions based on processing program 231 stored in memory 23.

Clock 20 performs a function to count time. Display 21 shows information such as time. Speaker 22 provides alarm sound as notification sound. Communication device 24 is an interface for communication with an external apparatus (for example, server 6 and terminal 8) over network 4. LED 25 is turned on in response to an instruction and lights up an area around sleep alarm apparatus 2. Microphone 28 accepts external audio input. Input device 29 includes various operation buttons.

Doppler sensor 30 implements at least a part of a sensing unit, and emits radio waves (microwaves) to a measurement target to contactlessly sense a signal (reflected waves) depending on motion of the measurement target (typically, a user).

(a3: Server 6)

Figure 3:
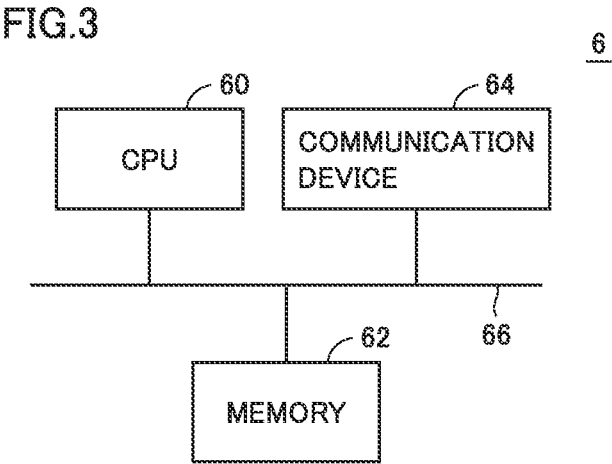
FIG. 3 is a schematic block diagram showing a basic configuration of a server according to the present embodiment.

FIG. 3 is a schematic block diagram showing a basic configuration of server 6 according to the present embodiment. Referring to FIG. 3, server 6 includes a CPU 60, a memory 62, a communication device 64, and an internal bus 66. Components are connected through internal bus 66.

CPU 60 represents one of processors and corresponds to an information processing unit for implementing various types of information processing performed in server 6. CPU 60 performs various types of information processing by using memory 62.

Various programs executed in server 6 are stored in memory 62. Though FIG. 3 illustrates an example in which memory 62 serves as a storage contained in server 6, for example, a storage medium attachable to and removable from server 6 such as an optical disc or a cartridge may be applicable or both of the storage and the storage medium as such may be applicable.

Communication device 64 is an interface for communication with an external apparatus (for example, sleep alarm apparatus 2 and terminal 8) over network 4.

(a4: Terminal 8)

Figure 4:
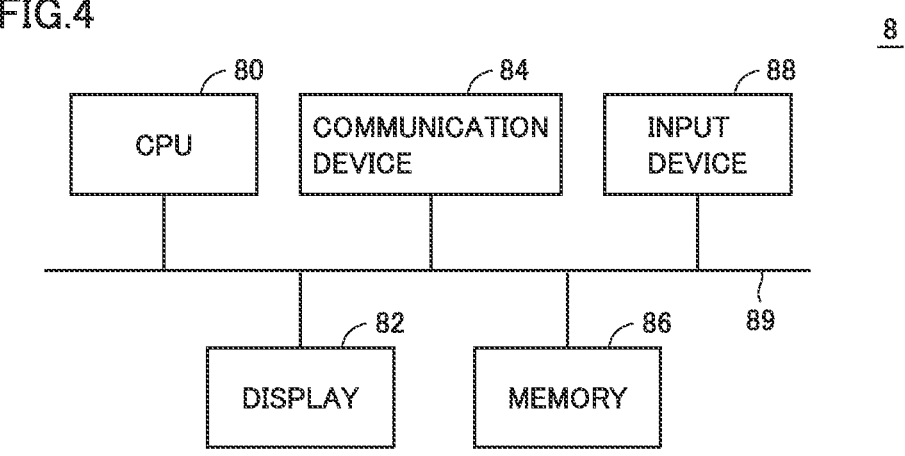
FIG. 4 is a schematic block diagram showing a basic configuration of a terminal according to the present embodiment.

FIG. 4 is a schematic block diagram showing a basic configuration of terminal 8 according to the present embodiment. Referring to FIG. 4, terminal 8 includes a CPU 80, a display 82, a communication device 84, a memory 86, an input device 88, and an internal bus 89. Components are connected through internal bus 89.

CPU 80 represents one of processors and corresponds to an information processing unit for implementing various types of information processing performed in terminal 8. CPU 80 performs various types of information processing by using memory 86.

Various programs executed in terminal 8 are stored in memory 86. Though FIG. 4 illustrates an example in which memory 86 serves as a storage contained in terminal 8, for example, a storage medium attachable to and removable from terminal 8 such as a memory card may be applicable or both of the storage and the storage medium as such may be applicable.

Communication device 84 is an interface for communication with an external apparatus (for example, sleep alarm apparatus 2 and server 6) over network 4.

Input device 88 includes any button, key, touch panel, and the like.

[B. Form of Use of Sleep Alarm Apparatus 2]

One exemplary form of use of sleep alarm apparatus 2 according to the present embodiment will now be described.

Figure 5:
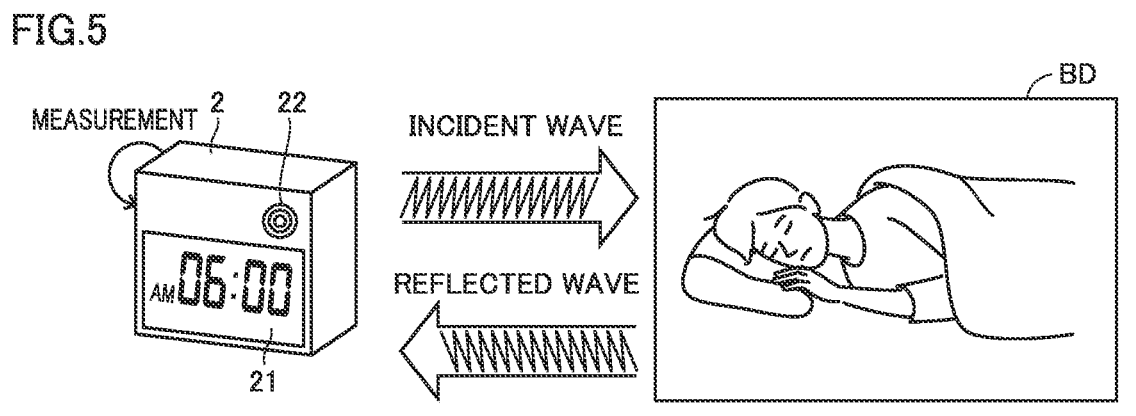

FIG. 5 is a schematic diagram showing an exemplary form of use of sleep alarm apparatus 2 according to the present embodiment. Referring to FIG. 5, sleep alarm apparatus 2 is arranged adjacently to a bed BD or the like of a user.

Sleep alarm apparatus 2 emits incident waves from Doppler sensor 30 to the user and receives reflected waves that may be produced by reflection of the incident waves at the user. Then, sleep alarm apparatus 2 measures various types of information on the user based on the emitted incident waves and the received reflected waves. A region of observation by sleep alarm apparatus 2 corresponds to a prescribed region (a prescribed area) in bed BD of the user.

Sleep alarm apparatus 2 may perform a clock function and an alarm function. In this case, sleep alarm apparatus 2 may provide alarm sound from speaker 22 when the notification condition is satisfied. On display 21, "AM 6:00" is shown as the current time counted by clock 20, by way of example.

[C. Functional Configuration]

A functional configuration of sleep alarm apparatus 2 according to the present embodiment will now be described. Sleep alarm apparatus 2 can measure various types of information on a user with Doppler sensor 30.

Various types of information on a user include (1) a distance to the user, (2) magnitude of motion of the user, (3) a sleep state of the user, (4) a lying state of the user, (5) whether or not the user is in a ready-to-sleep state, (6) whether the user is in a fallen-asleep state, and the like. Various types of processing are performed by making use of such information. All of these pieces of information do not have to be measured, and a function to measure information as appropriate should only be implemented as necessary.

Figure 6:
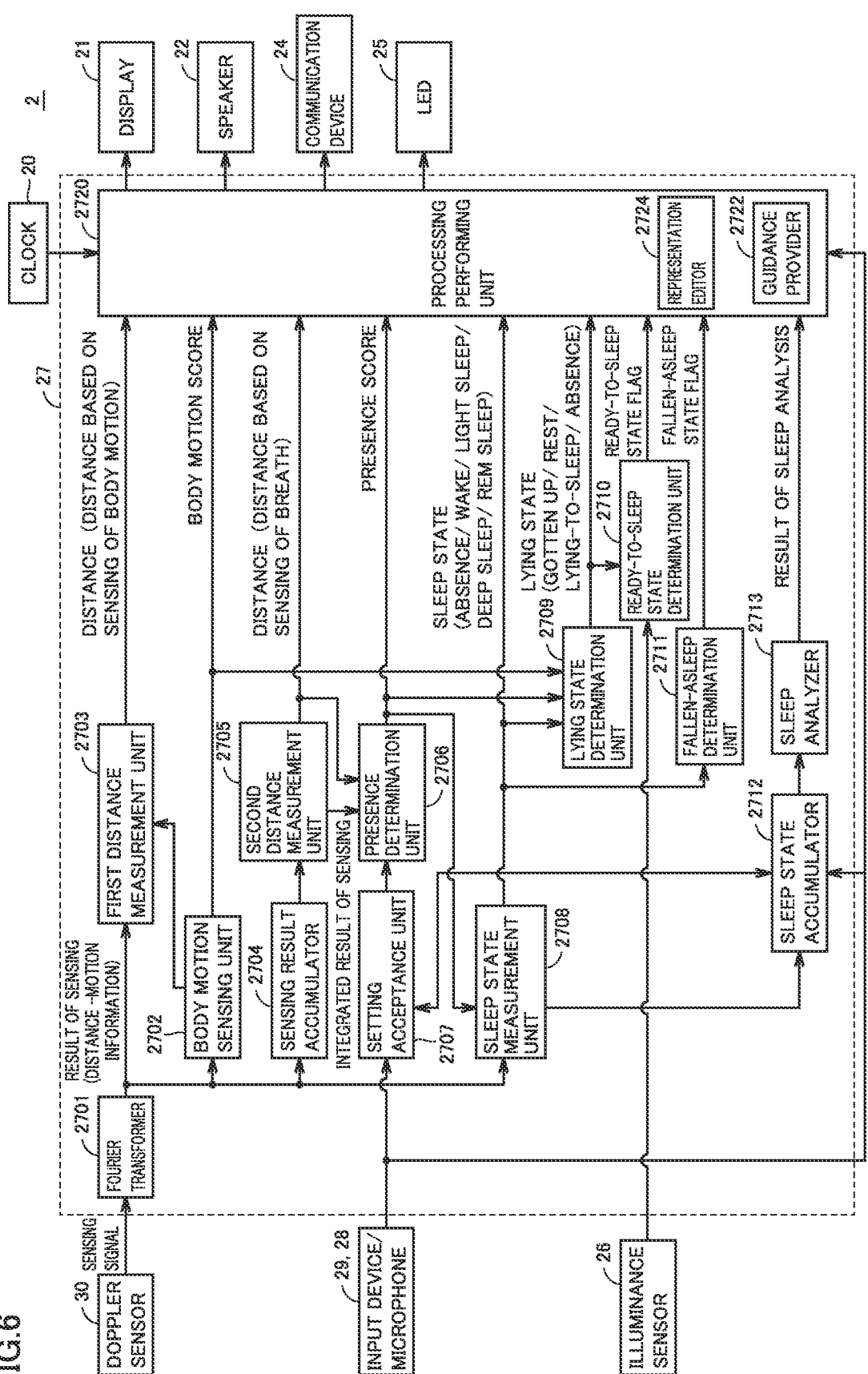
FIG. 6 is a schematic diagram showing an exemplary functional configuration of the sleep alarm apparatus according to the present embodiment.

FIG. 6 is a schematic diagram showing an exemplary functional configuration of sleep alarm apparatus 2 according to the present embodiment. Referring to FIG. 6, sleep alarm apparatus 2 obtains or calculates information necessary for performing various types of processing relating to sleep as will be described later. More specifically, sleep alarm apparatus 2 includes, as its functional configuration, a Fourier transformer 2701, a body motion sensing unit 2702, a first distance measurement unit 2703, a sensing result accumulator 2704, a second distance measurement unit 2705, a presence determination unit 2706, a setting acceptor 2707, a sleep state measurement unit 2708, a lying state determination unit 2709, a ready-to-sleep state determination unit 2710, a fallen-asleep determination unit 2711, a sleep state accumulator 2712, a sleep analyzer 2713, and a processing performing unit 2720.

These functions may be implemented by execution of processing program 231 stored or developed in memory 23 by CPU 27 of sleep alarm apparatus 2 in a predetermined order. Each function included in sleep alarm apparatus 2 will be described below in detail.

(c1: Doppler Sensor 30 and Fourier Transformer 2701)

Sleep alarm apparatus 2 according to the present embodiment may be configured to sense in real time with Doppler sensor 30, a distance to a measurement target (typically, a user) present in a measurement area and motion of the measurement target.

Doppler sensor 30 emits incident waves to the measurement target and receives reflected waves that may be produced by reflection of the incident waves at the measurement target. By making use of such a phenomenon that a frequency of the incident waves is varied to a frequency of reflected waves as a result of motion of the measurement target, motion of the user is sensed. A continuous wave (CW) scheme and a frequency modulated continuous wave (FMCW) scheme have been known as schemes for measurement using Doppler sensor 30. Though any scheme may be adopted in the present embodiment, processing under the FMCW scheme will be described as a typical example.

Figures 7A, 7B:
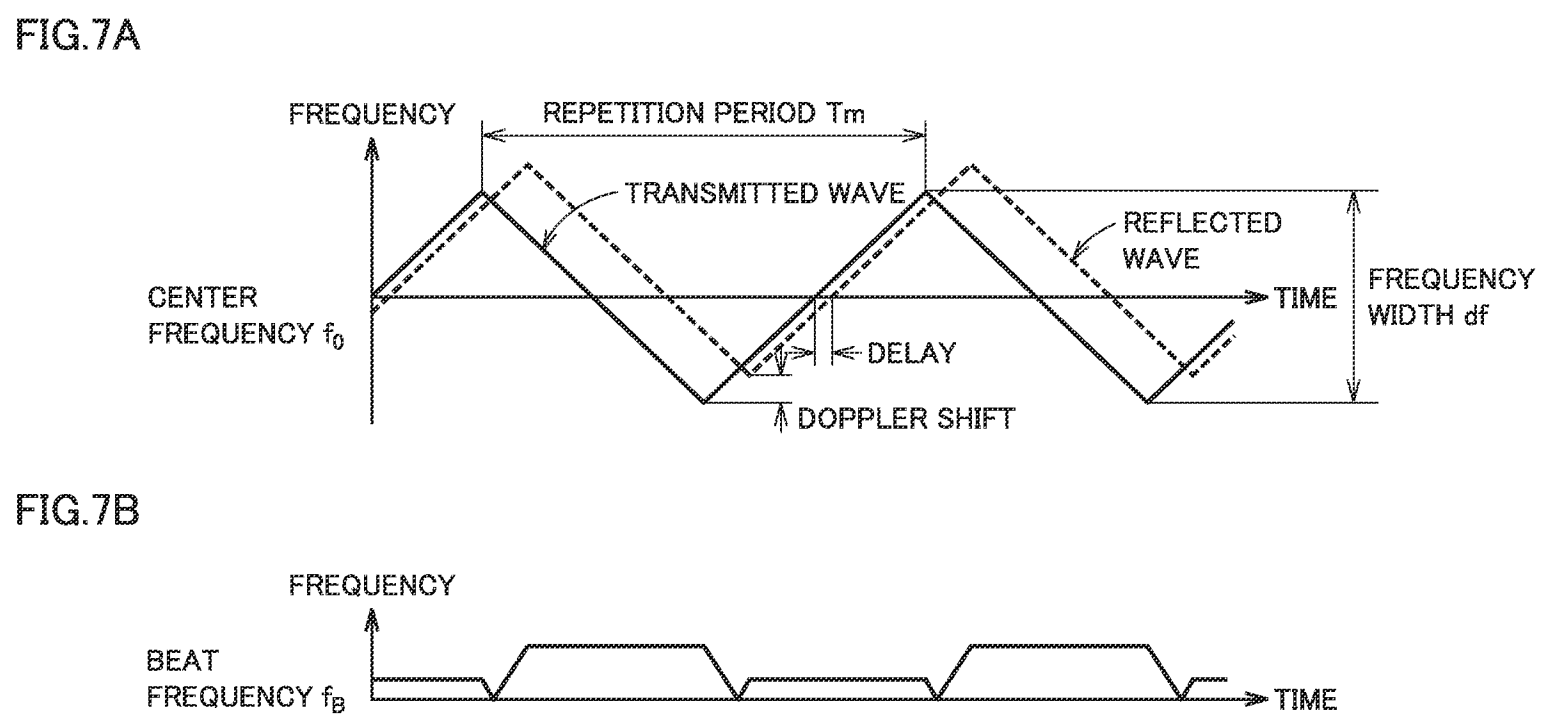

FIGS. 7A and 7B are diagrams for illustrating a scheme for measurement with Doppler sensor 30 of sleep alarm apparatus 2 according to the present embodiment. Referring to FIG. 7A, a frequency of incident waves emitted from Doppler sensor 30 is repeatedly varied (swept) every prescribed period. FIG. 7A shows an example of monotonous variation (monotonous increase and monotonous decrease) within a range of a frequency width df every repetition period $T_m$ with a center frequency $f_0$ being defined as the center. In other words, FIGS. 7A and 7B show such a waveform that the frequency is varied like a sawtooth.

By varying such a frequency, a frequency of reflected waves is also varied as following such variation. Magnitude of delay between the incident waves and the reflected waves and magnitude of a frequency difference (Doppler shift) between the incident waves and the reflected waves are varied depending on a distance to the measurement target (that is, a position of the measurement target with Doppler sensor 30 being defined as the reference) and motion.

A mixer within Doppler sensor 30 mixes transmitted waves and reflected waves so that a sensing signal at an intermediate frequency is provided. The provided sensing signal includes as its main component, a beat frequency $f_B$ as shown in FIG. 7B. Beat frequency $f_B$ corresponds to a frequency difference between the transmitted waves and the reflected waves, and reflects a distance to the measurement target and motion of the measurement target. As a result of Fourier transform of a time waveform of the sensing signal mainly composed of beat frequency $f_B$, information representing the distance to the measurement target and magnitude of motion of the measurement target can be obtained.

Figure 8:
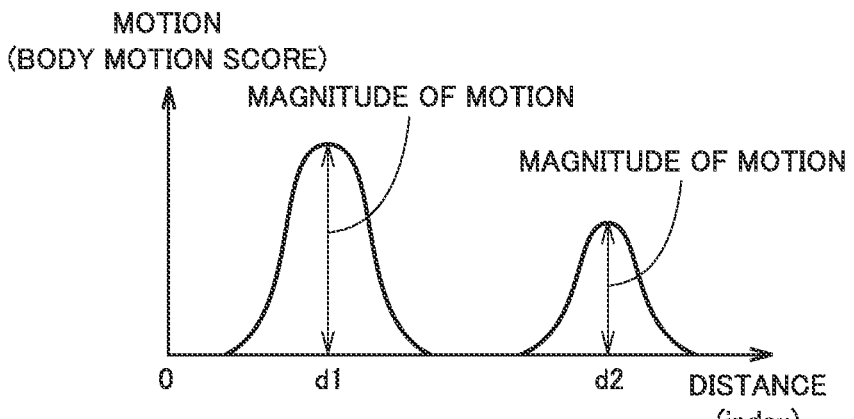
FIG. 8 is a diagram showing an exemplary result of Fourier transform of a sensing signal from the Doppler sensor of the sleep alarm apparatus according to the present embodiment.

FIG. 8 is a diagram showing an exemplary result of Fourier transform of a sensing signal from Doppler sensor 30 of sleep alarm apparatus 2 according to the present embodiment. Referring to FIG. 8, as a result of Fourier transform of the sensing signal from Doppler sensor 30, a result of sensing (distance-motion information) showing relation between the distance and motion can be obtained. More specifically, in a result of Fourier transform shown in FIG. 8, the abscissa represents a distance and the ordinate represents magnitude of motion. Though FIG. 8 continuously shows the distance and magnitude of motion, magnitude of motion may also be defined for each section delimited at every prescribed distance. In the description below, a number that identifies each section may also be called an "index".

In the exemplary result of sensing shown in FIG. 8, two peaks appear; a position of each peak represents the distance and a height of each peak represents magnitude of motion. It can be seen in the example shown in FIG. 8 that the measurement target is present at positions at a distance d1 and a distance d2.

Fourier transformer 2701 subjects sensing signals over a prescribed period from Doppler sensor 30 to Fourier transform. Though any approach can be adopted as a Fourier transform approach, fast Fourier transform (FFT) may typically be adopted. A time waveform obtained in a section where a frequency is increased and a time waveform obtained in a section where a frequency is decreased may separately be treated as a sensing signal to be subjected to Fourier transform. For example, only a single time waveform or only a set of time waveforms obtained in the section where the frequency is increased in a repetition period shown in FIGS. 7A and 7B may be subjected to Fourier transform, or only a single time waveform or only a set of time waveforms obtained in the section where the frequency is decreased in the repetition period shown in FIGS. 7A and 7B may be subjected to Fourier transform.

The result of Fourier transform (distance-motion information) provided from Fourier transformer 2701 is updated every repetition period or every integer multiple of the repetition period. In the description below, each of results of Fourier transform (distance-motion information) may also be referred to as a "frame".

Fourier transformer 2701 may be incorporated in a part of Doppler sensor 30. Therefore, the sensing unit that measures a distance to the user and/or motion of the user may be configured with a single Doppler sensor 30 alone or may include both of Doppler sensor 30 and Fourier transformer 2701. Alternatively, a plurality of Doppler sensors 30 may be adopted.

(c2: Body Motion Sensing Unit 2702)

Sleep alarm apparatus 2 according to the present embodiment may be able to detect with Doppler sensor 30, relatively large body motion such as turn-over or an operation to wave a hand. Distinction from slight motion due to breath or heartbeat of the user can be made, for example, based on an amount of change between incident waves and reflected waves or periodicity.

Relatively large motion of the user such as turn-over or an operation to wave a hand is herein called "body motion," and such motion, together with slight motion such as breath or heartbeat, may be called "motion".

Sleep alarm apparatus 2 may further be configured to be able to sense magnitude of body motion of the user based on a sensing signal from Doppler sensor 30 depending on motion of the user. In the description below, an indicator that indicates magnitude of body motion of the user may also be referred to as a "body motion score."

The body motion score is an indicator that indicates a probability of occurrence of relatively large motion of a body of the user (an operation to get in the bed or turn-over). In the present embodiment, as the user moves the body to a larger extent, a value of the body motion score is also larger.

Body motion sensing unit 2702 (FIG. 6) specifies a peak at which magnitude of motion is maximum by referring to a result of Fourier transform (distance-motion information) provided from Fourier transformer 2701 and provides magnitude of motion at the specified peak as magnitude of body motion of the user (a body motion score). For example, the body motion score may be provided as a value normalized to be within a range including a decimal between 0 and 1.

In order to enhance accuracy in sensing, determination as presence of body motion of the user may be made only when magnitude of motion at the specified peak exceeds a predetermined threshold value, and that magnitude may be provided as magnitude of body motion of the user. In other words, when magnitude of motion of the specified peak is equal to or smaller than the predetermined threshold value, body motion of the user (the body motion score) may be determined as zero.

When the FMCW scheme as shown in FIG. 8 is employed, intensity of the signal (that is, magnitude of motion) at each distance is calculated, a peak present in the relation between the calculated distance and magnitude of motion is detected, and the body motion score is determined based on magnitude of motion at that peak.

(c3: First Distance Measurement Unit 2703 and Second Distance Measurement Unit 2705)

Sleep alarm apparatus 2 according to the present embodiment may be configured to measure a distance to a user who is a measurement target, based on an output from Doppler sensor 30. At least one of two types of measurement methods by making use of magnitude of motion as will be described below can be adopted as such a method of measuring a distance to a user.

More specifically, at least one of a method (first distance measurement unit 2703) of measuring a distance with body motion of a user being focused on and a method (sensing result accumulator 2704 and second distance measurement unit 2705) of measuring a distance with breathing by a user being focused on can be adopted. In other words, at least one of first distance measurement unit 2703 and second distance measurement unit 2705 corresponds to the distance measurement unit that measures a distance to the user based on the output from Doppler sensor 30.

(i) First Distance Measurement Unit 2703

As shown in FIG. 8, first distance measurement unit 2703 specifies a peak that appears in a result of sensing (distance-motion information) representing relation between a distance and motion provided from Fourier transformer 2701 as a distance at which body motion of the user is sensed, and provides that distance as the distance to the user (which is denoted as a "distance (a distance based on sensing of body motion)" in FIG. 6).

By measuring a distance with such body motion of the user being focused on, a distance can be measured quickly and highly accurately.

(ii) Sensing Result Accumulator 2704 and Second Distance Measurement Unit 2705

Second distance measurement unit 2705 measures a distance with slight motion such as breathing by the user being focused on. Since a component of motion produced by breathing by the user is normally relatively small, it is difficult to measure the component for each frame. Then, second distance measurement unit 2705 achieves improved measurement accuracy by using a result of sensing (distance-motion information) over a plurality of frames.

Figure 9:
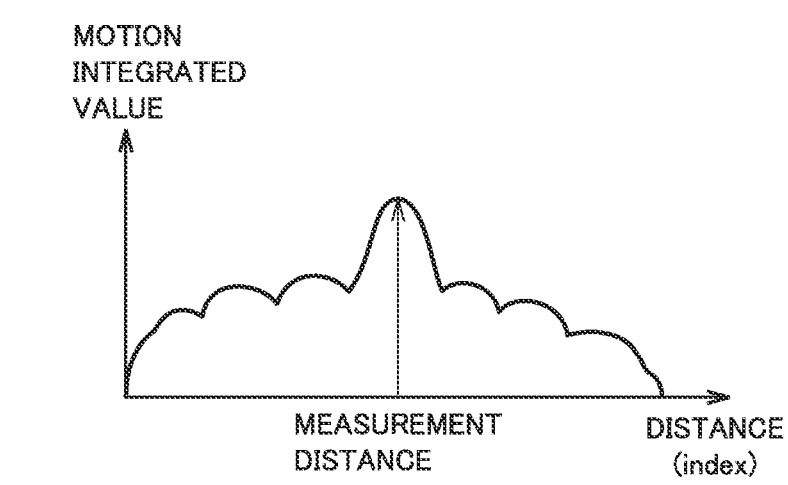
FIG. 9 is a diagram for illustrating a method of measuring a distance with breathing by a user being focused on, in the sleep alarm apparatus according to the present embodiment.

FIG. 9 is a diagram for illustrating a method of measuring a distance with breathing by a user being focused on, in sleep alarm apparatus 2 according to the present embodiment. Referring to FIG. 9, by integrating for each distance, a result of sensing (distance-motion information) obtained during each prescribed period, an integrated result of sensing can be calculated. For example, results of sensing obtained during a prescribed period that lasts for several seconds to more than ten seconds may be integrated.

Then, by referring to the calculated integrated result of sensing, a peak at which magnitude of an integrated motion value is maximum may be specified, and a distance corresponding to the specified peak may be provided as the measured distance (the distance based on sensing of breath). Alternatively, magnitude of the specified peak may be provided as a value representing slight motion.

More specifically, sensing result accumulator 2704 accumulates a result of sensing for each frame over a prescribed period. By implementing sensing result accumulator 2704, for example, with a ring buffer, it can hold a result of sensing in each frame only for a period during which the result of sensing should be accumulated, and can automatically erase the result of sensing for each frame by subsequently overwriting the result of sensing with a new result of sensing. Second distance measurement unit 2705 obtains a graph of an integrated motion value as in FIG. 9, by integrating for each distance, magnitude of motion based on results of sensing over the prescribed period accumulated in sensing result accumulator 2704. Then, a value of a distance (index) corresponding to the peak of the integrated motion value is adopted as the distance (the distance based on sensing of breath).

By using such an integrated result of sensing obtained by integrating the results of sensing over a plurality of frames, even in a situation that body motion is less, the distance to the user can accurately be measured. In other words, even slight motion of the user can be measured.

(c4: Presence Determination Unit 2706)

Sleep alarm apparatus 2 according to the present embodiment may be configured to determine whether or not a user is present in a measurement area based on an output from Doppler sensor 30. Presence determination unit 2706 calculates a "presence score" as an indicator for determining whether or not a user is present in the measurement area. Presence determination unit 2706 determines whether or not a user is present based on a measurement result (an integrated result of sensing) from second distance measurement unit 2705.

The presence score refers to an indicator that indicates a probability of presence of a user within a measurement area based on calculation of magnitude of motion in the measurement area (or in a predetermined effective measurement area or an effective measurement area arbitrarily set by a user) based on an output from Doppler sensor 30. For example, the presence score may be provided as a value normalized to be within a range including a decimal between 0 and 1.

Sleep alarm apparatus 2 according to the present embodiment makes use of a new finding that, in an environment where a user is not present, a characteristic waveform appears in a graph of an integrated result of sensing calculated by second distance measurement unit 2705.

Figure 10:
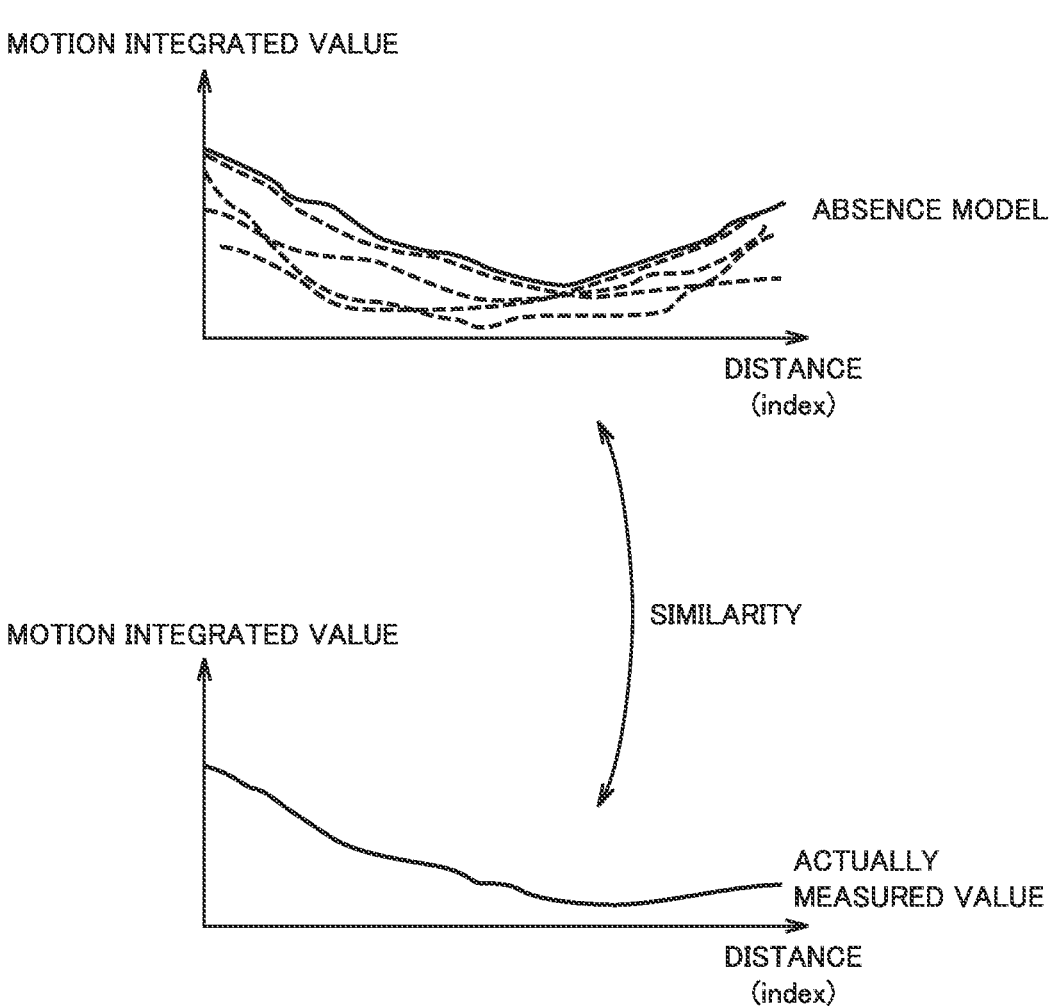
FIG. 10 is a diagram for illustrating a method of calculating a presence score in the sleep alarm apparatus according to the present embodiment.

FIG. 10 is a diagram for illustrating a method of calculating a presence score in sleep alarm apparatus 2 according to the present embodiment. Referring to FIG. 10, in some bedrooms different in size, shape, or the like, actual measurement is conducted while no user is present, and an integrated result of sensing in each environment is calculated. For a graph of each calculated integrated result of sensing, an absence model is determined in advance by adopting for each distance a largest integrated motion value among the integrated motion values shown in each graph and preparing a graph including each adopted value.

By comparing the absence model thus prepared with the integrated result of sensing obtained in actual measurement and evaluating similarity between their shapes, the presence score is calculated. Similarity may be calculated by normalizing each of the absence model and the integrated result of sensing.

When the absence model is designed such that the presence score exhibits a larger value as possibility of presence of the user in the measurement area is higher, the presence score exhibits a smaller value as similarity between the absence model and the integrated result of sensing is higher.

Therefore, when the similarity and the presence score are both normalized to be within a range including a decimal between 0 and 1, the presence score can be calculated as the presence score=(1−similarity).

Though an example in which the presence score is calculated based on similarity in shape to the absence model is given in the description above, instead of such a method of determining similarity, the presence score may be high when the integrated result of sensing obtained in actual measurement is equal to or smaller than a value in the absence model at a large number of positions (index).

An example in which a user other than a user who is a measurement target is present in the measurement area is also assumed. In this case, measurement for the user other than the user who is the measurement target is conducted. Then, an effective measurement area may be set in order to focus only on a specific user as a measurement target. The effective measurement area is smaller than the measurement area within which a distance can be measured.

Setting acceptor 2707 accepts from a user, setting of the effective measurement area in accordance with an input from a user through input device 29 or microphone 28. Though a default effective measurement area may be set in advance, the effective measurement area may arbitrarily be set or modified by means of setting acceptor 2707.

Presence determination unit 2706 determines a user state as absence when the distance (the distance based on sensing of breath) measured by second distance measurement unit 2705 indicates being out of the effective measurement area.

Normally, the effective measurement area is set within a prescribed distance (for example, 100 cm) from sleep alarm apparatus 2. When the measured distance to the user exceeds this distance, the presence score is fixed to "0". Only one or both of an upper limit and a lower limit of the distance from sleep alarm apparatus 2 may be defined for the effective measurement area. An example in which the upper limit of the distance from sleep alarm apparatus 2 is set is basically described below.

Figure 11A:
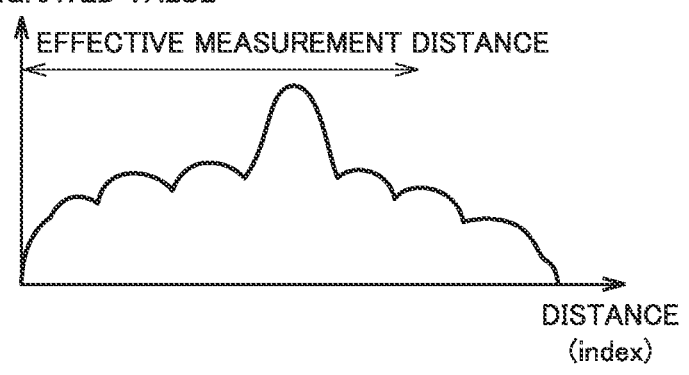
FIGS. 11A and 11B are diagrams for illustrating relation between an effective measurement area and a presence score in the sleep alarm apparatus according to the present embodiment.
Figure 11B:
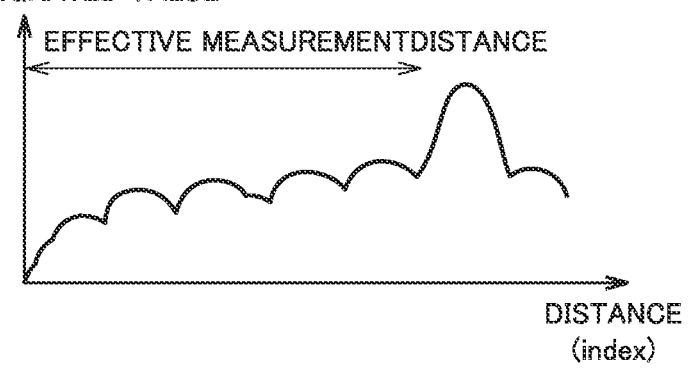

FIGS. 11A and 11B are diagrams for illustrating relation between the effective measurement area and the presence score in sleep alarm apparatus 2 according to the present embodiment. FIG. 11A shows an example in which a position (index) of a peak that appears in an integrated result of sensing is present within the effective measurement area. In the example shown in FIG. 11A, the presence score exhibits some value (≠0) which represents possibility of presence of a user.

In contrast, FIG. 11B shows an example in which a position (index) of a peak that appears in an integrated result of sensing is present out of the effective measurement area. In the example shown in FIG. 11B, though possibility of presence of the user in the measurement area is high, the user can be determined as not being present within the effective measurement area, and hence the presence score is fixed to "0". In other words, presence determination unit 2706 determines the user as not being present unless the measured distance (the distance (the distance based on sensing of breath)) to the user is within the effective measurement area.

By setting such an effective measurement area, for example, in an example where a user who is the measurement target and a user who is not the measurement target lies within the measurement area of sleep alarm apparatus 2, such a situation that the user who is the measurement target gets up earlier and measurement for the remaining user who is not the measurement target is continued to consequently provide an incorrect measurement result can be avoided.

(c5: Sleep State Measurement Unit 2708)

Sleep alarm apparatus 2 according to the present embodiment may be configured to measure in real time, a sleep state of a user based on an output from Doppler sensor 30. More specifically, sleep state measurement unit 2708 (FIG. 6) measures in real time, a sleep state of a user based on an output from Doppler sensor 30.

The sleep state of the user may include, for example, five types of absence, wake/presence, light sleep, deep sleep, and REM sleep. The sleep state may be categorized into a smaller or larger number of types.

Typically, sleep state measurement unit 2708 may be implemented by using a trained model created in advance by using a machine learning approach. In this case, incident waves are emitted from Doppler sensor 30 to any subject to obtain a sensing signal (or a result of sensing obtained by Fourier transform of the sensing signal), and in parallel, measurement for the subject with a known approach is conducted to obtain a value representing the sleep state. By tagging the value representing the sleep state corresponding to the sensing signal or the result of sensing, the trained model can be generated, and by using the generated trained model, a trained model can be generated with a known approach.

By using the trained model created with such an arbitrary method, sleep state measurement unit 2708 that measures in real time the sleep state of the user based on an output from Doppler sensor 30 can be implemented.

Though FIG. 6 illustrates a configuration in which a result of sensing (distance-motion information) provided from Fourier transformer 2701 is provided to sleep state measurement unit 2708, without being limited as such, the sensing signal from Doppler sensor 30 may directly be provided to sleep state measurement unit 2708.

The presence score calculated by presence determination unit 2706 is provided to sleep state measurement unit 2708. The presence score refers to an indicator for determining whether or not the user is present within the measurement area (or the effective measurement area). When a value of the presence score is smaller than a predetermined threshold value (for example, 0.05), "absence" may forcibly be provided as the sleep state. As described above, presence determination unit 2706 provides an effective presence score only when the user is present within the effective measurement area, based on the distance measured by second distance measurement unit 2705. By making use of such a presence score, sleep state measurement unit 2708 can measure the sleep state, with the user present within the effective measurement area smaller than the measurement area within which second distance measurement unit 2705 can conduct measurement being focused on, based on a measurement result from second distance measurement unit 2705. In other words, measurement by mistake of the sleep state of a user who is present out of the effective measurement area can be prevented.

Though FIG. 6 shows an exemplary configuration in which "absence" is provided as the sleep state when the value of the presence score calculated by presence determination unit 2706 is smaller than a predetermined threshold value, without being limited as such, any configuration capable of measuring the sleep state with the user present within the effective measurement area being focused on may be adopted. For example, only a component within the effective measurement area in the result of sensing (distance-motion information) provided from Fourier transformer 2701 may be made use of to measure the sleep state.

By adopting sleep state measurement unit 2708 as above, the sleep state of the user can be measured in real time with Doppler sensor 30.

(c6: Lying State Determination Unit 2709)

Sleep alarm apparatus 2 according to the present embodiment may be configured to determine a lying state of the user based on an output from Doppler sensor 30. The lying state may include, for example, four types of gotten-up, rest, lying-to-sleep, and absence.

Typically, lying state determination unit 2709 determines which lying state a state falls under, based on the presence score, the body motion score, the sleep state (absence, wake, light sleep, deep sleep, and REM sleep), and the user state (moving, non-moving, and absence).

FIG. 12 is a diagram for illustrating a method of determining a lying state in sleep alarm apparatus 2 according to the present embodiment.

Referring to FIG. 12, lying state determination unit 2709 holds a state machine SM corresponding to each state of the lying state. Specifically, state machine SM includes an absent state ST1, a gotten-up state ST2, a resting state ST3, and a lying-to-bed state ST4.

For absent state ST1, transition TR1 to gotten-up state ST2 is defined. For gotten-up state ST2, transition TR2 to absent state ST1, transition TR5 to resting state ST3, and transition TR8 to lying-to-bed state ST4 are defined. For resting state ST3, transition TR3 to absent state ST1, transition TR6 to gotten-up state ST2, and transition TR9 to lying-to-sleep state ST4 are defined.

Each condition for transition will be described below.

Transition TR1 from absent state ST1 to gotten-up state ST2 is made on condition that the user has gotten up. For example, satisfying any of a state continued for a prescribed period that a value of the presence score exceeds a predetermined threshold value TH1 (for example, 0.95) and the sleep state falling under "wake (wake/presence)" may be adopted as the transition condition. Threshold value TH1 may be determined based on a range of values of the presence score at which possibility of presence of the user is considered as being sufficiently high.

Transition TR2 from gotten-up state ST2 to absent state ST1 is made on condition that the user is not present. For example, satisfying a state continued for a prescribed period that the value of the presence score is smaller than a predetermined threshold value TH2 (for example, 0.05) may be adopted as the transition condition. Threshold value TH2 may be determined based on a range of values of the presence score at which possibility of absence of the user is considered as being sufficiently high.

Transition TR3 from resting state ST3 to absent state ST1 and transition TR4 from lying-to-sleep state ST4 to absent state ST1 may be made under a condition similar to that for transition TR2.

Transition TR5 from gotten-up state ST2 to resting state ST3 is typically made on condition that a rest determination condition CND1 is satisfied. Transition TR6 from resting state ST3 to gotten-up state ST2 is typically made on condition that rest determination condition CND1 is not satisfied.

Rest determination condition CND1 includes two states, and it is satisfied when body motion of the user is relatively small and not satisfied when body motion of the user is relatively large. More specifically, under rest determination condition CND1, transition to "satisfied" is made when the value of the body motion score is smaller than a threshold value TH4 in a state "not satisfied" and the state that the value of the presence score exceeds threshold value TH1 continues for a prescribed period. When the value of the body motion score exceeds a threshold value TH3 in a state "satisfied" or when the value of the presence score becomes smaller than threshold value TH1, transition to "not satisfied" is made.

Threshold value TH3 may be determined based on a range of values of the body motion score at which body motion of the user is considered as being sufficiently large. Threshold value TH4 may be determined based on a range of values of the body motion score at which body motion of the user is considered as being sufficiently small.

In other words, satisfying rest determination condition CND1 means that the user is present and body motion of the user is sufficiently small. Rest determination condition CND1 not being satisfied means that body motion of the user is sufficiently large or the user is absent.

Transition TR8 from gotten-up state ST2 to lying-to-sleep state ST4 and transition TR9 from resting state ST3 to lying-to-sleep state ST4 is typically made on condition that a lying-to-sleep determination condition CND 2 is satisfied. Transition TR7 from lying-to-sleep state ST4 to gotten-up state ST2 is typically made on condition that lying-to-sleep determination condition CND2 is not satisfied or the sleep state falls under "wake (wake/presence)."

Lying-to-sleep determination condition CND2 includes two states, and it is satisfied when the user is estimated to be lying to sleep, and not satisfied otherwise. More specifically, under lying-to-sleep determination condition CND2, transition to "satisfied" is made when a state that the sleep state falls under sleep (any of light sleep, deep sleep, and REM sleep) continues for a prescribed period in the state "not satisfied." Transition to "not satisfied" is made when the sleep state falls under a state (that is, absence or wake) other than sleep (any of light sleep, deep sleep, and REM sleep) in the state "satisfied".

As set forth above, lying state determination unit 2709 successively makes determination as to the transition condition in accordance with each state to determine which of the four states the state falls under.

Instead of implementing state machine SM itself as shown in FIG. 12, such a form of implementation as successively updating a state flag based on each transition condition may be adopted.

Since both of sleep state measurement unit 2708 and lying state determination unit 2709 provide a state "absence", information from one or both of them may selectively be used depending on a situation.

(c7: Ready-to-Sleep State Determination Unit 2710)

Sleep alarm apparatus 2 according to the present embodiment may be configured to determine whether or not the user is in a ready-to-sleep state based on an output from Doppler sensor 30. Ready-to-sleep state determination unit 2710 sets/resets a ready-to-sleep state flag indicating whether or not the user is in the ready-to-sleep state.

The ready-to-sleep state means a state that the user is ready to lie to sleep or the user is going to lie to sleep. The ready-to-sleep state may include, for example, a state that the user is in bed or a state that the user is at rest on the bed. Furthermore, a state toward lying to sleep with turn-off or dimming of light based on an ambient environment sensed by illuminance sensor 26 may be defined as a further condition.

Typically, ready-to-sleep state determination unit 2710 determines whether or not the ready-to-sleep state has been set based on information on the lying-to-sleep state (lying to sleep, rest, wake, and absence) measured by lying state determination unit 2709 and/or the ambient environment sensed by illuminance sensor 26. Ready-to-sleep state determination unit 2710 sets/resets the ready-to-sleep state flag in accordance with a result of determination.

(c8: Fallen-Asleep Determination Unit 2711)

Sleep alarm apparatus 2 according to the present embodiment may be configured to determine whether or not the user has fallen asleep based on an output from Doppler sensor 30. Fallen-asleep determination unit 2711 sets/resets a fallen-asleep state flag indicating whether or not the user has fallen asleep.

Typically, fallen-asleep determination unit 2711 determines whether or not the user has fallen asleep based on the sleep state of the user provided from sleep state measurement unit 2708. Specifically, when the sleep state of the user falls under any of light sleep, deep sleep, and REM sleep, the user is determined as being in the fallen-asleep state, and the fallen-asleep state flag is set (activated).

(c9: Sleep State Accumulator 2712 and Sleep Analyzer 2713)

Sleep state accumulator 2712 accumulates the sleep state measured by sleep state measurement unit 2708 over a prescribed period. In addition to the sleep state measured by sleep state measurement unit 2708, relevant information may also be accumulated.

Sleep analyzer 2713 analyzes the sleep state accumulated in sleep state accumulator 2712 and relevant information. Sleep analyzer 2713 calculates, for example, a sleep fulfillment degree of the user who is sleeping.

(c10: Processing Performing Unit 2720)

Sleep alarm apparatus 2 according to the present embodiment uses various types of information obtained in processing as described above to perform various types of processing as will be described later. Processing performing unit 2720 performs various types of processing by using the distance measured with body motion of the user being focused on, the distance measured with breathing by the user being focused on, the body motion score, the presence score, the sleep state, the lying state, the ready-to-sleep state flag, the fallen-asleep state flag, a result of analysis of sleep, and the like.

As processing performing unit 2720 performs various types of processing, display 21, speaker 22, communication device 24, LED 25, and the like may be driven.

Processing performing unit 2720 includes a guidance provider 2722 that assists setting of the effective measurement area and a representation editor 2724 that has a result of measurement of the sleep state of the user shown and accepts an edition operation by the user onto the result of measurement. Details of functions provided by guidance provider 2722 and representation editor 2724 will be described later.

[D. Processing Relating to Effective Measurement Area]

Processing relating to the effective measurement area (accepted by setting acceptor 2707 in FIG. 6) in sleep alarm apparatus 2 according to the present embodiment will now be described.

(d1: Application)

Figure 13A:
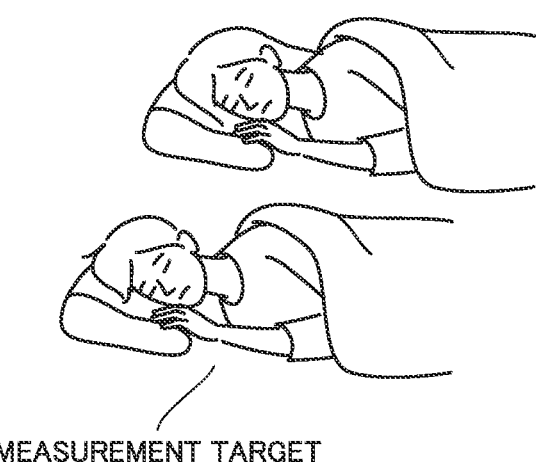
FIGS. 13A and 13B are diagrams for illustrating exemplary prevention of erroneous measurement by making use of an effective measurement area in the sleep alarm apparatus according to the present embodiment.
Figure 13B:

FIGS. 13A and 13B are diagrams for illustrating exemplary prevention of erroneous measurement by making use of the effective measurement area in sleep alarm apparatus 2 according to the present embodiment. Referring to FIG. 13A, a situation that two users sleep side by side is assumed. A user on a lower side in the figure is defined as the target of measurement by sleep alarm apparatus 2.

In such a situation, as shown in FIG. 13B, the user who is the measurement target may leave the bed. In this case, when a user who is not the measurement target is still present within the area of measurement by sleep alarm apparatus 2, sleep alarm apparatus 2 regards the user who is not basically the measurement target as the measurement target and continues measurement.

By appropriately setting the effective measurement area as described above, possibility of such erroneous measurement can be lowered.

(d2: Processing in Operation)

Processing in operation of sleep alarm apparatus 2 according to the present embodiment will now be described.

Figure 14:
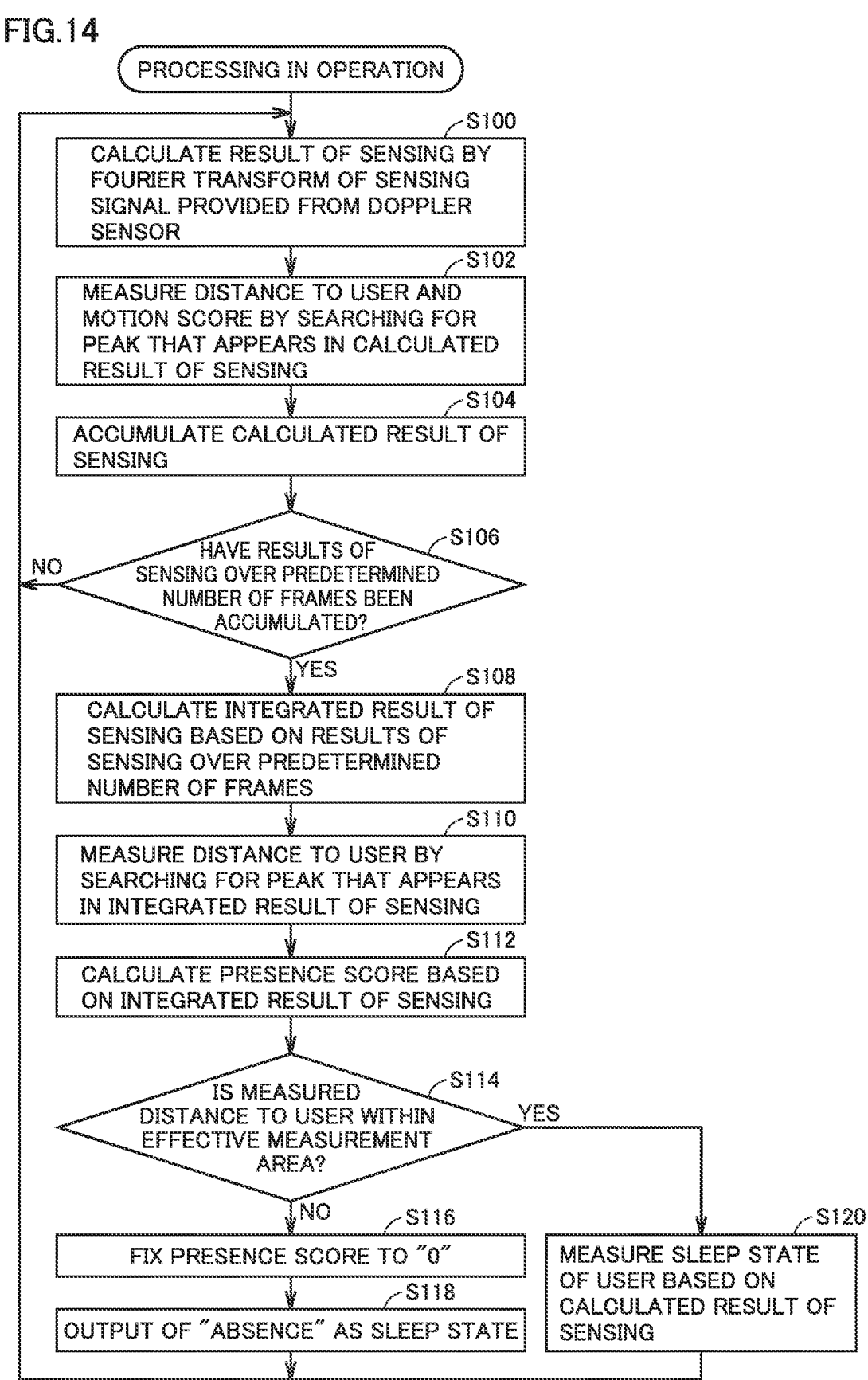
FIG. 14 is a flowchart showing processing in operation of the sleep alarm apparatus according to the present embodiment.

FIG. 14 is a flowchart showing processing in operation of sleep alarm apparatus 2 according to the present embodiment. Each step shown in FIG. 14 is typically implemented by execution by CPU 27 of sleep alarm apparatus 2, of processing program 231 stored in memory 23.

Referring to FIG. 14, sleep alarm apparatus 2 calculates a result of sensing representing relation between a distance and motion (distance-motion information) by Fourier transform of a sensing signal provided from Doppler sensor 30 (step S100).

Sleep alarm apparatus 2 measures a distance to the user (distance at which motion of the user is sensed) and a motion score representing magnitude of motion of the user by searching for a peak that appears in the calculated result of sensing (distance-motion information) (step S102).

In succession, sleep alarm apparatus 2 accumulates the calculated result of sensing (distance-motion information) (step S104) and determines whether or not results of sensing over a predetermined number of frames have been accumulated (step S106).

When the results of sensing over the predetermined number of frames have been accumulated (YES in step S106), sleep alarm apparatus 2 calculates an integrated result of sensing from the results of sensing over the predetermined number of frames (step S108). Sleep alarm apparatus 2 measures the distance to the user (the distance measured with breathing by the user being focused on) by searching for a peak that appears in the calculated integrated result of sensing (step S110). Sleep alarm apparatus 2 calculates the presence score based on the calculated integrated result of sensing (step S112).

Furthermore, sleep alarm apparatus 2 determines whether or not the measured distance to the user (the distance measured with breathing by the user being focused on) is within a predetermined effective measurement area (step S114). When the measured distance to the user (the distance measured with breathing by the user being focused on) is not within the predetermined effective measurement area (NO in step S114), sleep alarm apparatus 2 fixes the presence score to "0" (step 5116) and provides "absence" as the sleep state (step S118). Then, processing in step S100 or later is repeated.

When the measured distance to the user (the distance measured with breathing by the user being focused on) is within the predetermined effective measurement area (YES in step S114), sleep alarm apparatus 2 measures the sleep state of the user based on the calculated result of sensing (distance-motion information) (step S120). Then, processing in step S100 or later is repeated.

When the results of sensing over the predetermined number of frames have not been accumulated (NO in step S106), processing in steps S108 to S120 is skipped and processing in step S100 or later is repeated.

(d3: Processing at the Time of Initial Setting)

Processing at the time of initial setting of sleep alarm apparatus 2 according to the present embodiment will now be described.

Sleep alarm apparatus 2 includes guidance provider 2722 (FIG. 6) that assists initial setting by a user. Guidance provider 2722 may provide guidance that assists adjustment in advance of relative positional relation between a position where sleep alarm apparatus 2 is placed and a position where the user will lie during sleep. Any of visual guidance and aural guidance may be adopted.

Figure 15A:
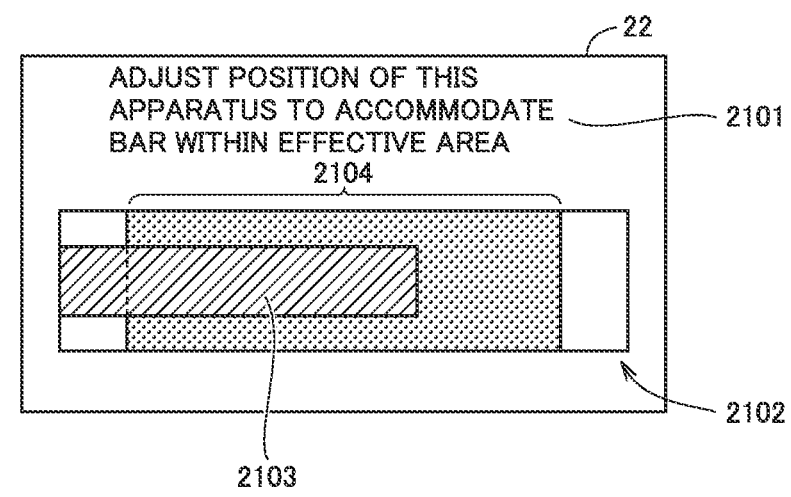
FIGS. 15A and 15B are schematic diagrams showing exemplary guidance for assisting determination of a position of arrangement in the sleep alarm apparatus according to the present embodiment.
Figure 15B:
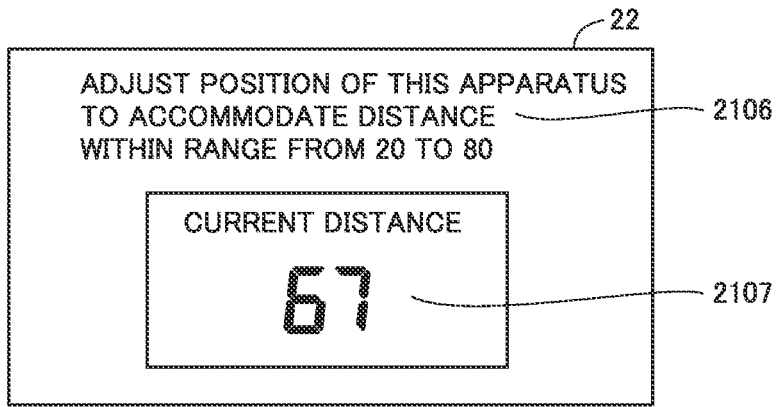

FIGS. 15A and 15B are schematic diagrams showing one example of guidance for assisting determination of a position of arrangement in sleep alarm apparatus 2 according to the present embodiment. FIGS. 15A and 15B show examples in which guidance representing whether or not a position where the user lies is within the effective measurement area is provided.

In FIGS. 15A and 15B, a distance from sleep alarm apparatus 2 to the user is shown in real time. For showing a distance, typically, a distance with body motion of the user being focused on that is measured in real time by first distance measurement unit 2703 (FIG. 6) is used. The user adjusts relative positional relation between a position where the user himself/herself lies and a position of arrangement of sleep alarm apparatus 2 in accordance with guidance as shown in FIGS. 15A and 15B.

FIG. 15A illustrates guidance in which the distance to the user is shown with bar representation. A bar 2103 having a length in accordance with a successively measured distance to the user is shown on display 21 of sleep alarm apparatus 2 in correspondence with a measurement area representation 2102 showing an area (a measurement area) within which sleep alarm apparatus 2 can measure the distance. An effective measurement area representation 2104 showing a predetermined effective measurement area is shown in association with measurement area representation 2102. The user adjusts the position of sleep alarm apparatus 2 or the position where the user himself/herself lies such that bar 2103 is accommodated within effective measurement area representation 2104 in accordance with a guidance message 2101. By providing the user with such guidance, appropriate measurement in sleep alarm apparatus 2 can be conducted.

FIG. 15B illustrates guidance in which the distance to the user is shown with a numeric value. A numeric value 2107 representing the successively measured distance to the user is shown on display 21 of sleep alarm apparatus 2. The user adjusts the position of sleep alarm apparatus 2 or the position where the user himself/herself lies such that numeric value 2107 is accommodated within a designated range in accordance with a guidance message 2106. By providing the user with such guidance, appropriate measurement in sleep alarm apparatus 2 can be conducted.

Though FIGS. 15A and 15B show examples in which guidance is visually provided on display 21 of sleep alarm apparatus 2 as typical examples, guidance may aurally be provided through speaker 22 of sleep alarm apparatus 2 or together with speaker 22 of sleep alarm apparatus 2. In this case, output of a voice message relating to the distance to the user or the like may be provided from speaker 22.

Alternatively, by transmitting information or a command for providing guidance from sleep alarm apparatus 2 to terminal 8, guidance may be provided on display 82 of terminal 8. Furthermore, an output of a voice message may be provided from a not-shown speaker or the like of terminal 8.

Guidance provider 2722 may thus provide output of at least one of an image and sound that indicates whether or not a position where the user lies during sleep is within the effective measurement area.

For a function relating to guidance described below as well, similarly, information can visually or aurally be provided to the user in at least one of sleep alarm apparatus 2 and terminal 8.

(d4: Processing at the Time of Setting of Effective Measurement Area)

Processing at the time of setting of the effective area of measurement by sleep alarm apparatus 2 according to the present embodiment will now be described.

Though a default effective measurement area may be set in advance, the effective measurement area may arbitrarily be set or modified by the user. Guidance for the user to arbitrarily set or change the effective measurement area may be provided.

By way of example, a result of measurement of the distance to the user may be used to set the effective measurement area.

Figure 16:
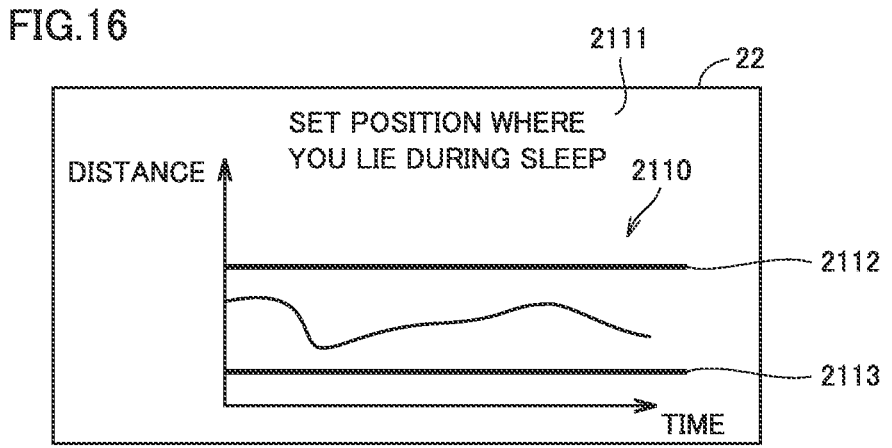
FIG. 16 is a schematic diagram showing one example of guidance for assisting setting of an effective measurement area in the sleep alarm apparatus according to the present embodiment.

FIG. 16 is a schematic diagram showing one example of guidance for assisting setting of the effective measurement area in sleep alarm apparatus 2 according to the present embodiment. In guidance shown in FIG. 16, a graph 2110 that shows change over time in distance measured at the time when the user actually lies to sleep or the distance measured at the time when the user lies to sleep on a trial basis is shown. Representation in a graph 2210 may successively be updated in accordance with the distance measured in real time.

The user sets the effective measurement area by adjusting an upper limit setting bar 2112 and a lower limit setting bar 2113 by referring to the distance shown in graph 2110, in accordance with guidance message 2101. Contents of this setting are given to presence determination unit 2706 through setting acceptor 2707 (see FIG. 6).

Though FIG. 16 shows both of upper limit setting bar 2112 and lower limit setting bar 2113, only any one of them may be shown. By providing such guidance to the user, request for input of the position where the user lies during sleep can be issued to the user.

In another example, the number of persons who lie in the same sleep area (for example, one bed) may be set. Specifically, the effective measurement area may be changed as appropriate in accordance with whether a single user or a plurality of users may simultaneously lie within the area of measurement by sleep alarm apparatus 2.

Figure 17:
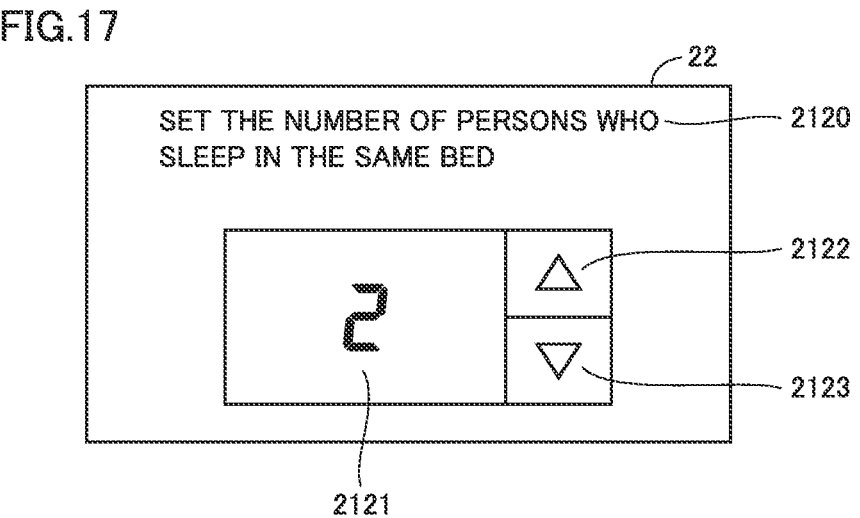
FIG. 17 is a schematic diagram showing another example of guidance for assisting setting of the effective measurement area in the sleep alarm apparatus according to the present embodiment.

FIG. 17 is a schematic diagram showing another example of guidance for assisting setting of the effective measurement area in sleep alarm apparatus 2 according to the present embodiment. In guidance shown in FIG. 17, guidance for accepting setting of the number of persons who lie in the same sleep area is provided.

The user sets a numeric value 2121 representing the number of persons who lie in the same sleep area to an actual value, by selecting an increase button 2122 or a decrease button 2123 in accordance with guidance message 2120. Setting acceptor 2707 may set the effective measurement area as appropriate in accordance with the number of persons set in response to the guidance as shown in FIG. 17 and provide the effective measurement area to presence determination unit 2706 (see FIG. 6). By providing such guidance to the user, request for input of the number of users who sleep can be issued to the user.

Furthermore, input of a size of a bed (a length such as cm or a bed size such as single/semidouble/double) may be accepted to set the effective measurement area in consideration also of provided information.

By providing the user with guidance as shown in FIGS. 16 and 17, the effective measurement area can appropriately be set.

(d5: Processing in Reviewing Setting of Effective Measurement Area)

Processing in reviewing setting of the effective area of measurement by sleep alarm apparatus 2 according to the present embodiment will now be described.

The effective measurement area set in a procedure as described above may be reviewed as appropriate in accordance with a result of actual measurement. For example, the effective measurement area may be changed based on a result of measurement of the sleep state of the user.

Figure 18:
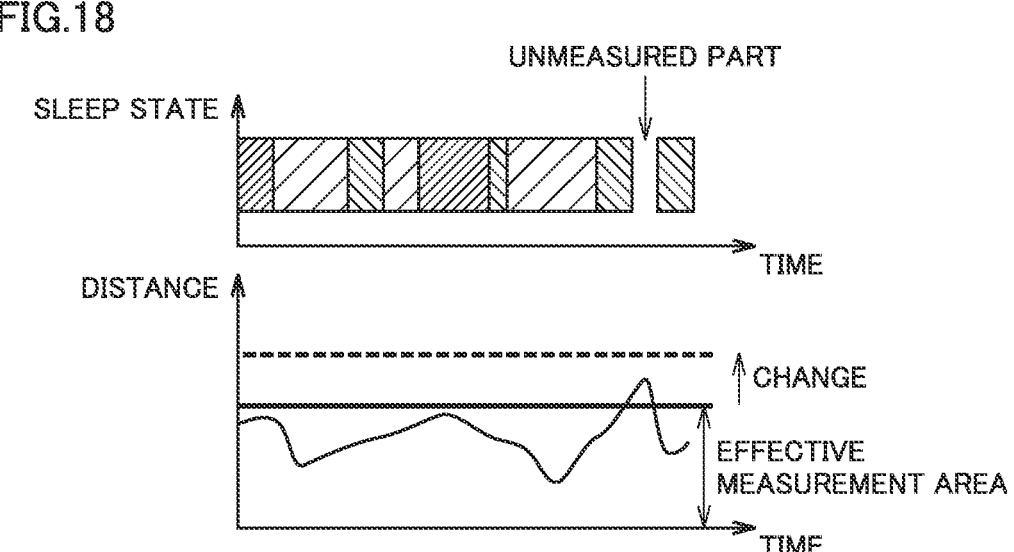
FIG. 18 is a diagram for illustrating one example of processing for reviewing setting of the effective measurement area in the sleep alarm apparatus according to the present embodiment.

FIG. 18 is a diagram for illustrating one example of processing for reviewing setting of the effective measurement area in sleep alarm apparatus 2 according to the present embodiment. Referring to FIG. 18, an example in which the sleep state could not be measured in a specific section (generation of an unmeasured part) in the result of measurement of the sleep state of the user is assumed.

One of factors for occurrence of such an unmeasured part is that the user was not present within the effective measurement area. Therefore, setting of the effective measurement area may be changed by bringing chronological data on the sleep state of the user in correspondence with chronological data on the distance to the user and referring to the distance in the section corresponding to the unmeasured part.

In the example shown in FIG. 18, in the section of the unmeasured part, the distance to the user is beyond the previously set effective measurement area. Therefore, the effective measurement area can be adjusted such that the distance to the user measured in that section is accommodated therein. Such adjustment of the effective measurement area can be made by setting acceptor 2707 referring to the result of measurement of the sleep state stored in sleep state accumulator 2712 (see FIG. 6).

Sleep alarm apparatus 2 according to the present embodiment can provide the user with the result of measurement of the sleep state and can also change the result of measurement of the sleep state in accordance with an operation by the user.

For example, when the user moves out of the effective measurement area due to turn-over or the like, "absence" is recorded as the result of measurement of the sleep state. In such a case, the user may manually correct the result of measurement to a value indicating that the user actually lies to sleep.

Figure 19:
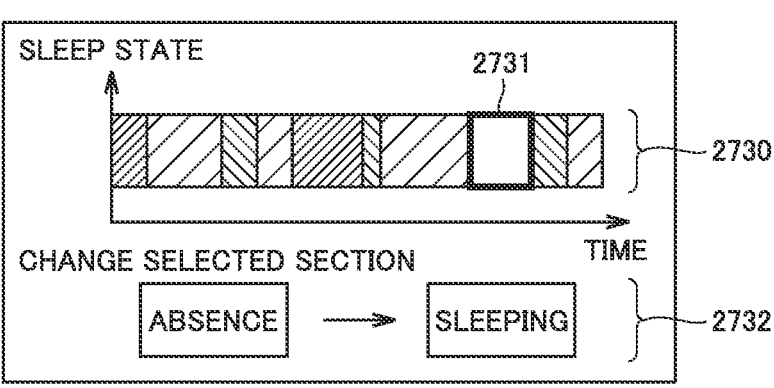
FIG. 19 is a diagram for illustrating another example of processing for reviewing setting of the effective measurement area in the sleep alarm apparatus according to the present embodiment.

FIG. 19 is a diagram for illustrating another example of processing for reviewing setting of the effective measurement area in sleep alarm apparatus 2 according to the present embodiment. Referring to FIG. 19, representation editor 2724 (FIG. 6) of sleep alarm apparatus 2 has a result 2730 of measurement of the sleep state of the user shown. The result may be shown on display 21 of sleep alarm apparatus 2 or display 82 of terminal 8. Furthermore, result 2730 of measurement of the sleep state of the user may be provided in such a manner that the measurement result is stored in server 6 and any information processing apparatus such as a personal computer or a smartphone may access server 6.

A change operation portion 2732 for arbitrarily changing result 2730 of measurement of the sleep state of the user in a selected section 2731 arbitrarily selected by the user may be provided. FIG. 19 shows an example in which a value of the sleep state in selected section 2731 selected in result 2730 of measurement is changed from "absence" to "sleeping". Thus, representation editor 2724 has the result of measurement of the sleep state of the user shown and accepts an edition operation by the user onto the result of measurement.

The effective measurement area may be changed in response to the edition operation onto the result of measurement of the sleep state. As shown in FIG. 19, in response to change in value of the sleep state from "absence" to "sleeping", the effective measurement area may be changed based on the distance to the user measured in a corresponding section. A method of changing the effective measurement area or the like is as described with reference to FIG. 18 above. Setting acceptor 2707 may thus change the effective measurement area in accordance with the edition operation accepted by representation editor 2724.

Through the processing procedure as above, the effective measurement area can appropriately be set again.

[E. Advantage]

According to the present embodiment, a new configuration in which the distance to the user in addition to the sleep state of the user is measured is provided. According to such a configuration, the identical Doppler sensor can be used to measure in real time, the distance to the user and the sleep state of the user. Therefore, processing making use of results of measurement of both of the distance to the user and the sleep state of the user can be implemented.

While certain example systems, methods, devices, and apparatuses have been described herein, it is to be understood that the appended claims are not to be limited to the systems, methods, devices, and apparatuses disclosed, but on the contrary, are intended to cover various modifications and equivalent arrangements included within the spirit and scope of the appended claims.

The invention claimed is:

1. An information processing apparatus, comprising:
a sensing unit including a sensor configured to sense a subject by emitting incident waves and receiving reflected waves produced by reflection of the incident waves;
a processor; and
a memory storing computer readable instructions that, when executed by the processor, cause the information processing apparatus to at least:
generate, for display, a user interface for receiving an input from the user associated with a positional relation between a position where the information processing apparatus is placed and a position where the user lies during sleep, wherein
the sensing unit is placed on a surface at a position separate from the position where the user lies during sleep, and
the user interface is configured to display a first distance associated with the positional relation between the position where the information processing apparatus is placed and the position where the user lies during sleep;
set the first distance based on the positional relation between the position where the information processing apparatus is placed and the position where the user lies during sleep;
measure a distance to the user based on an output from the sensor; and determine the user as not being present when the measured distance to the user exceeds the first distance, wherein the first distance is shorter than a measurable maximum distance.

2. The information processing apparatus according to claim 1, wherein the information processing apparatus is further caused to determine the user as not being present based on the measured distance to the user not being within an area set based on the first distance and a second distance shorter than the first distance.

3. The information processing apparatus according to claim 2, wherein the user interface includes representation showing the first distance and the second distance for setting the area.

4. The information processing apparatus according to claim 2, wherein the information processing apparatus is further caused to provide output of at least one of an image and sound that indicates whether the position where the user lies is within the area.

5. The information processing apparatus according to claim 2, wherein the information processing apparatus is further caused to accept setting of the area from the user.

6. The information processing apparatus according to claim 5, wherein the information processing apparatus is further caused to request for input of at least one of a position where the user lies during sleep and the number of persons who lie therein.

7. The information processing apparatus according to claim 5, wherein the information processing apparatus is further caused to change the area based on a result of measurement of a sleep state of the user.

8. The information processing apparatus according to claim 7, wherein the information processing apparatus is further caused to:

represent the result of measurement of the sleep state of the user and accept an edition operation by the user onto the result of measurement, and change the area in response to the accepted edition operation.

9. The information processing apparatus according to claim 1, wherein the information processing apparatus is further caused to calculate an amount of motion at each distance from the sensor, based on the output from the sensor, and estimate a distance at which the amount of motion is largest as the distance to the user.

10. The information processing apparatus according to claim 9, wherein the information processing apparatus is further caused to focus, as the amount of motion, on motion by breathing by the user.

11. The information processing apparatus according to claim 2, wherein the information processing apparatus is further caused to measure a sleep state of the user based on the output from the sensor.

12. The information processing apparatus according to claim 11, wherein the information processing apparatus is further caused to measure the sleep state of the user who is present within the area, based on a result of measurement of the distance.

13. The information processing apparatus according to claim 2, wherein the information processing apparatus is further caused to:

calculate a body motion score and a presence score based on the output from the sensor, the body motion score being an indicator that indicates magnitude of body motion of the user, the presence score being an indicator for determining whether the user is present in the area; and determine a lying state of the user based on the body motion score and the presence score.

14. The information processing apparatus according to claim 13, wherein the information processing apparatus is further caused to calculate, based on the output from the sensor, the presence score in accordance with a position of a peak that appears in relation between the distance to the user and the magnitude of motion of the user.

15. The information processing apparatus according to claim 1, wherein the user interface is configured to receive input from the user associated with a bed size, and the first distance is determined based on the input associated with the bed size.

16. The information processing apparatus according to claim 1, further comprising a display configured to display the user interface, wherein the display is integrated with the sensing unit.

17. The information processing apparatus according to claim 1, wherein the distance, between the position where the information processing apparatus is placed and the position where the user lies during sleep, is adjustable by the user.

18. An information processing method implemented via an information processing apparatus having a sensing unit including a sensor configured to sense a subject by emitting incident waves and receiving reflected waves produced by reflection of the incident waves, the information processing method comprising:

generating, for display, a user interface for receiving an input from the user associated with a positional relation between a position where the information processing apparatus is placed and a position where the user lies during sleep, wherein the user interface is configured to display a first distance associated with the positional relation between the position where the information processing apparatus is placed and the position where the user lies during sleep;

setting the first distance based on the positional relation between the position where the information processing apparatus is placed and the position where the user lies during sleep;

measuring a distance to the user based on the output from the sensor; and determining the user as not being present when the measured distance to the user exceeds the first distance, wherein the first distance is shorter than a measurable maximum distance.

19. A non-transitory computer-readable storage medium having stored therein instructions that, when executed by a processor of an information processing apparatus, including a sensor configured to sense a subject by emitting incident waves and receiving reflected waves produced by reflection of the incident waves, cause the information processing apparatus to provide execution comprising:

generating, for display, a user interface for receiving an input from the user associated with a positional relation between a position where the information processing apparatus is placed and a position where the user lies during sleep, wherein the user interface is configured to display a first distance associated with the positional relation between the position where the information processing apparatus is placed and the position where the user lies during sleep;

setting the first distance based on the positional relation between the position where the information processing apparatus is placed and the position where the user lies during sleep;

measuring a distance to the user based on an output from the sensor; and determining the user as not being present when the measured distance to the user exceeds the first distance, wherein the first distance is shorter than a measurable maximum distance.

20. An information processing system, comprising:

a sensor configured to sense a subject by emitting incident waves and receiving reflected waves produced by reflection of the incident waves; and a control device having at least a processor and a memory, wherein the control device is configured to at least:

generate, for display, a user interface for receiving an input from the user associated with a positional relation between a position where the information processing system is placed and a position where the user lies during sleep, wherein the user interface is configured to display a first distance associated positional relation between the position where the information processing apparatus is placed and the position where the user lies during sleep;

set the first distance based on the position tween the position where the information processing apparatus is placed and the position where the user lies during sleep;

measure a distance to the user based on an output from the sensor; and determine the user as not being present when the measured distance to the user exceeds the first distance, wherein the first distance is shorter than a measurable maximum distance.

* * * * *